Oct. 8, 1957 H. C. SWIM Plant Pat. 1,652
NECTARINE TREE
Filed Nov. 6, 1956
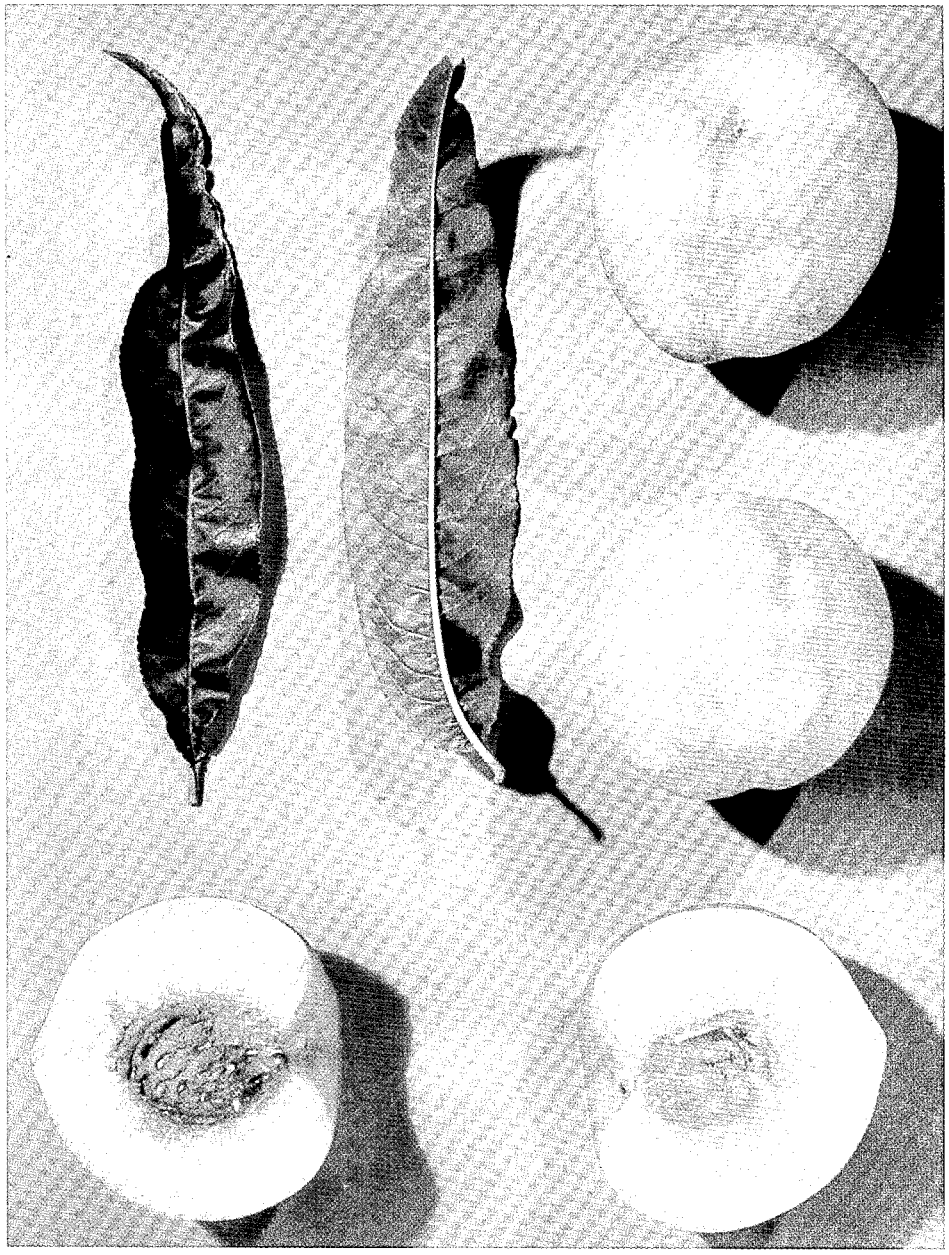
Inventor.
H. C. Swim
By: Robb & Robb
Attorneys.

United States Patent Office

Plant Pat. 1,652
Patented Oct. 8, 1957

1,652

NECTARINE TREE

Herbert C. Swim, Ontario, Calif., assignor to Armstrong Nurseries, Inc., Ontario, Calif, a corporation of California Application November 6, 1956, Serial No. 620,781

1 Claim. (Cl. 47—62)

The present invention relates to a new and distinct variety of nectarine tree of the yellow-fleshed, freestone, fruit-bearing type, which was originated by me as the result of planting seed obtained from open-pollinated flowers on an unnamed and unpatented peach variety which in turn was produced from a cross of an unnamed and unpatented peach seedling of "Goldmine" nectarine (unpatented) × "Rio Oso Gem" peach (Plant Patent No. 84) and an unnamed and unpatented peach seedling of "Goldmine" nectarine × "July Elberta" peach (Plant Patent No. 15).

The primary objective of this breeding was to produce a new and improved nectarine variety having the fruit size and quality of the peach varieties constituting its antecedents.

The parent of my new nectarine variety was a well-colored, medium-sized, yellow-fleshed, freestone peach having a medium chilling requirement and ripening about mid-August in southern California.

The objective of this breeding, as noted above, was fully achieved in my new variety, as evidenced by the following unique combination of outstanding features:

(1) Large, yellow-fleshed, freestone fruit;

(2) High red blush of fruit skin, particularly on the side exposed to the sun;

(3) A low to medium winter chilling requirement, falling between "Panamint" nectarine (Plant Patent No. 1,100) and "Silver Lode" nectarine (Plant Patent No. 1,023) as observed in southern California; and (4) A ripening period in mid-August approximately 4 to 5 weeks after "Panamint" nectarine.

In comparison with its parent variety, my new nectarine differs therefrom primarily in being a nectarine, whereas the parent is a peach. It differs from its ancestral peach varieties "Rio Oso Gem" and "July Elberta" by being somewhat smaller than either, having a higher skin color than either, and being a nectarine instead of a peach. It also differs from "Goldmine" nectarine primarily by being somewhat larger and being yellow-fleshed, whereas "Goldmine" nectarine is white-fleshed. In respect to ripening dates, my new nectarine ripens about 3 weeks after "July Elberta" in southern California; about in the same period as "Rio Oso Gem"; and about a week to 10 days after "Goldmine" nectarine.

The foregoing characteristics and distinctions definitely differentiate my new variety from its parent, as well as from all other varieties of which I am aware, and asexual reproduction of the new variety by grafting, as performed at Ontario, California, shows that these characteristics and distinctions come true to form and are established and transmitted through succeeding propagations.

The accompanying drawing shows typical specimens of the foliage and fruit of my new variety, with both the upper and lower surfaces of the foliage being illustrated and both exterior and sectional views of the fruit being shown, all as depicted in color as nearly true as it is reasonably possible to make the same in a color illustration of this character.

The following is a detailed description of my new variety, as based upon observations of specimens grown at Ontario, California, with color terminology in accordance with Robert F. Wilson's Horticultural Colour Chart, except where color terminology is given from Ridgway's Color Standards and Nomenclature (hereafter abbreviated as "Ridgway") or where general color terms of ordinary dictionary significance are obvious:

Dates first and last picking: From August 5 to August 21, and from August 15 to August 30, respectively; usually ripens in mid-August in southern California, about 4 or 5 weeks after "Panamint" nectarine.

Tree: Medium size; medium vigor; upright; dense; round; productive; regular bearer.

*Trunk.*—Medium caliper; medium surface roughness.

*Branches.*—Medium caliper; medium smoothness; dull. Color—near Light Grayish Olive, Plate XLVI (Ridgway). Lenticels—medium number; medium size.

*Leaves.*—Acuminate; lanceolate; medium thickness; relatively smooth; wavy and crinkled type, as classified in publication by Meader and Blake entitled "Progress report on identification of peach varieties by leaf characteristics," appearing in American Society for Horticultural Science Proceedings for 1939, vol. 37, pages 203 to 207. Size—large; length—from 5½ inches to 7 inches; width—from 1 inch to 1⅜ inches. Color: upper surface—between Cress Green, Plate XXXI (Ridgway) and Dark Dull Yellow-Green, Plate XXXII (Ridgway); under surface—between Light Elm Green, Plate XVII (Ridgway) and Deep Dull Yellow-Green (1), Plate XXXII (Ridgway). Margin—finely serrate. Petiole—medium length; from ¼ inch to ½ inch in length; medium thickness. Glands—average 4 in number; alternate; medium size; mixed; usually positioned on petiole below attachment of leaf blade, but also sometimes positioned on leaf blade near attachment to petiole; color—green. Stipules—short; narrow; early deciduous.

Flower buds: From large to medium size; long; pointed; with yellowish pubescence on bud scales, and with grayish pubescence on outer surface of free portion of calyx.

Flowers:

*Dates of first and full bloom.*—Over prolonged period of observations, dates of first and full bloom varied widely from February 10 to March 12 and from February 18 to March 20, respectively, due to variations in weather conditions from year-to-year; considered from early to medium earliness as compared with other varieties.

*Size.*—From large to medium.

*Color.*—Near Carmine Rose, Plate 621, page 75.

Fruit:

*Maturity when described.*—Eating-ripe. Date—August 18.

*Size.*—Slightly variable; large. Axial diameter—from 2⅜ inches to 2⅝ inches. Transverse diameter in suture plane—from 2¼ inches to 2½ inches. Diameter at right angles to suture plane—from 2⅜ inches to 2⅝ inches.

*Form.*—Only slightly variable; symmetrical; globose.

*Suture.*—An inconspicuous line; extends from base to apex; has slight depression beyond pistil point.

*Ventral surface.*—Rounded slightly; lipped toward base; lips equal.

*Cavity.*—Rounded. Depth—from ¼ inch to ⅜ inch. Breadth—from ⅝ inch to ¾ inch.

*Base.*—Rounded.

*Apex.*—Short; rounded; with short, apical pistil point.

*Stem.*—From ¼ inch to ¾ inch in length; from medium caliper to stout; glabrous; from strong to medium adherence to stone.

*Skin.*—Thick; tough. Tendency to crack—slight. Color—between Indian Yellow, Plate 6/2, page 6 and Saffron Yellow, Plate 7/2, page 7, overlaid particularly on side exposed to the sun with between Mandarin Red, Plate 17/1, page 17 and Vermilion, Plate 18/1, page 18, and also overlaid with Cardinal Red, Plate 822, page 168 and Chrysanthemum Crimson, Plate 824/1, page 169. Down—wanting.

*Flesh.*—Color—between Indian Yellow, Plate 6/1, page 6 and Saffron Yellow, Plate 7/1, page 7, with flecks of near Geranium Lake, Plate 20/1, page 20. Surface of pit cavity—color—between Geranium Lake, Plate 20, page 20 and Carmine, Plate 21, page 21, with fibres of near Indian Yellow, Plate 6/1, page 6. Amygdalin—scant. Juice—moderate. Texture—firm; fine; meaty. Fibres—few; tender. Ripens—evenly. Flavor—subacid. Aroma—wanting. Eating quality—good.

Stone: Free; adheres to flesh somewhat along both dorsal and ventral edges; short fibres; free on sides; sometimes retains short fibre-like threads in furrows.

*Size.*—Large. Length—from 1⅜ inches to 1⅝ inches. Breadth—from 1 inch to 1¼ inches. Thickness—from ⅝ inch to ¾ inch.

*Form.*—Ovoid; cuneate toward apex.

*Base.*—Straight.

*Hilum.*—Narrow; oblong.

*Apex.*—Acute.

*Sides.*—Unequal; curved on right and left sides.

*Surface.*—Irregularly furrowed toward apex; ridged toward apex; pitted toward base.

*Ridges.*—Somewhat jagged.

*Pits.*—Elongated.

*Ventral edge.*—Thick; with wing throughout.

*Dorsal edge.*—Medium; with narrow groove throughout; ridges on either side interrupted.

*Tendency to split.*—Slight.

*Color.*—Between Sayal Brown, Plate XXIX (Ridgway) and Tawny Olive, Plate XXIX (Ridgway), with markings of near Carmine, Plate I (Ridgway).

Use: Market; local; dessert.

Keeping Quality: Medium.

Disease resistance: No disease susceptibility has been observed at Ontario, California.

Shipping quality: Medium.

I claim:

A new and distinct variety of nectarine tree of the yellow-fleshed, freestone, fruit-bearing type, substantially as herein shown and described, characterized particularly as to novelty by the large size of its fruit, the high red blush on the skin of the fruit, particularly on the side exposed to the sun, its relatively low to medium winter chilling requirement as grown in southern California, falling between "Panamint" nectarine (Plant Patent No. 1,100) and "Silver Lode" nectarine (Plant Patent No. 1,023), and by its mid-August ripening period falling from 4 to 5 weeks after that of the "Panamint" nectarine variety aforesaid.

No references cited.